United States Patent
Moreira De Almeida et al.

(10) Patent No.: US 9,649,328 B2
(45) Date of Patent: May 16, 2017

(54) ASSOCIATION OF BETA-GLUCANS AND ARABINOXYLANS

(71) Applicant: Generale Biscuit, Rungis (FR)

(72) Inventors: Isabel Moreira De Almeida, Sant Arnoult en Yvelines (FR); Alexandra Meynier, Dourdan (FR); Maria Urbieta, Madrid (ES)

(73) Assignee: Generale Biscuit, Clamart (FR)

( * ) Notice: Subject to any disclaimer, the term of this patent is extended or adjusted under 35 U.S.C. 154(b) by 201 days.

(21) Appl. No.: 14/395,630

(22) PCT Filed: Apr. 23, 2013

(86) PCT No.: PCT/EP2013/058388
§ 371 (c)(1),
(2) Date: Oct. 20, 2014

(87) PCT Pub. No.: WO2013/160300
PCT Pub. Date: Oct. 31, 2013

(65) Prior Publication Data
US 2015/0080336 A1   Mar. 19, 2015

(30) Foreign Application Priority Data

Apr. 23, 2012 (EP) ..................................... 12305466

(51) Int. Cl.
| | | |
|---|---|---|
| *A61K 31/717* | (2006.01) | |
| *A21D 13/02* | (2006.01) | |
| *A61K 31/716* | (2006.01) | |
| *A21D 13/00* | (2017.01) | |
| *A21D 13/04* | (2017.01) | |
| *A61K 36/8998* | (2006.01) | |
| *A21D 13/08* | (2006.01) | |
| *A23L 7/10* | (2016.01) | |
| *A23L 33/105* | (2016.01) | |
| *A23L 33/21* | (2016.01) | |
| *A23L 33/22* | (2016.01) | |

(52) U.S. Cl.
CPC ........ *A61K 31/717* (2013.01); *A21D 13/0025* (2013.01); *A21D 13/0041* (2013.01); *A21D 13/02* (2013.01); *A21D 13/04* (2013.01); *A21D 13/08* (2013.01); *A23L 7/10* (2016.08); *A23L 7/115* (2016.08); *A23L 33/105* (2016.08); *A23L 33/21* (2016.08); *A23L 33/22* (2016.08); *A61K 31/716* (2013.01); *A61K 36/8998* (2013.01); *A23V 2002/00* (2013.01)

(58) Field of Classification Search
None
See application file for complete search history.

(56) References Cited

U.S. PATENT DOCUMENTS

| 4,804,545 A | 2/1989 | Goering et al. |
|---|---|---|
| 4,873,098 A * | 10/1989 | Banks .................... A21D 13/08 426/549 |
| 5,024,996 A | 6/1991 | Ringe |
| 2010/0040736 A1 | 2/2010 | Van Haesendonck et al. |

FOREIGN PATENT DOCUMENTS

| JP | 2009039043 A | 2/2009 |
|---|---|---|
| KR | 20070076231 A | 7/2007 |
| RU | 2340184 C2 | 12/2008 |
| RU | 2467574 C2 | 2/2011 |
| RU | 2009126835 A | 2/2011 |
| WO | 2006002495 A1 | 1/2006 |
| WO | 2006005464 A2 | 1/2006 |
| WO | 2009003931 A1 | 1/2009 |
| WO | 2009005329 A2 | 1/2009 |
| WO | 2010020639 A1 | 2/2010 |

OTHER PUBLICATIONS

Izydorczyk, M. S., & Dexter, J. E. (2008). Barley β-glucans and arabinoxylans: molecular structure, physicochemical properties, and uses in food products—a review. Food Research International, 41(9), 850-868.*
Van Craeyveld, V., Swennen, K., Dornez, E., Van de Wiele, T., Marzorati, M., Verstraete, W., . . . & De Ketelaere, B. (2008). Structurally different wheat-derived arabinoxylooligosaccharides have different prebiotic and fermentation properties in rats. The Journal of nutrition, 138(12), 2348-2355.*
Search Report by Russia Federal Service for Intellectual Property, dated Jul. 27, 2015 (2 pgs.).
Trogh, I et al.; "The combined use of hull-less barley flour and xylanase as a strategy for wheat/hull-less barley flour breads with increased arabinoxylan and (1->3,1->4)-beta-D-glucan levels;" Journal of Cereal Science, Academic Press Ltd.; vol. 40, No. 3; Nov. 1, 2004; pp. 257-267 (11 pgs.).
Holguin-Acuna, A. L., et al; "Maize bran/oat flour extruded breakfast cereal: A novel source of complex polysaccharides and an antioxidant" Food Chemistry, Elsevier Ltd, NL; vol. 11, No. 3; Dec. 1, 2008; pp. 654-657 (4 pgs.).
Midilli, M. et al.; "The effects of supplementation of enzyme and probiotic to the rations on some blood parameters of broilers;" Indian Veterinary Journal, Madras, IN; vol. 81 No. 11; Nov. 1, 2004; pp. 1213-1216(4 pgs).
Haberer, B. et al.; "Effects of beta-glucanase and xylanase supplementation in pigs fed a diet rich in non starch polysaccharides: Composition of digesta in different prececal segments and postprandial time", Journal of Animal Physiology and Animal Nutrition, Blackwell, Berlin, DE; vol. 78, No. 2; Jan. 1, 1998; pp. 84-94 (11 pgs.).

(Continued)

*Primary Examiner* — Shaojia Anna Jiang
*Assistant Examiner* — Dale R Miller
(74) *Attorney, Agent, or Firm* — Fitch, Even, Tabin & Flannery LLP

(57) ABSTRACT

The present invention relates to an association of beta-glucans from a first cereal and arabinoxylans from a second cereal different from the first cereal, and their use to improve the microbiota balance in human gut.

11 Claims, 2 Drawing Sheets

(56) References Cited

OTHER PUBLICATIONS

Jacobs, M. S., et al.; "Evaluation of baking procedures for incorporation of barley roller milling fractions containing high levels of dietary fibre into bread;" Journal of the Science of Food and Agriculture, Wiley & Sons, Chichester, GB; vol. 88, No. 4; Mar. 1, 2008; pp. 558-568 (11 pgs.).

International Search Report and Written Opinion of the International Searching Authority, date of mailing Jun. 5, 2013 for PCT/EP2013/058388 (12 pgs.).

European Patent Office Communication dated Jul. 6, 2012 for Application No. 12305466.0 (8 pgs.).

\* cited by examiner

… (1)

ASSOCIATION OF BETA-GLUCANS AND ARABINOXYLANS

CROSS REFERENCE TO RELATED APPLICATIONS

This application is a U.S. national phase application of International Application No. PCT/EP2013/058388, filed Apr. 23, 2013, which claims benefit from Europe Application 12305466.0, filed Apr. 23, 2012, which are hereby incorporated herein by reference in their entirety.

FIELD

The present invention relates to an association of beta-glucans from a first cereal and arabinoxylans from a second cereal different from the first cereal, and their use to improve the microbiota balance in human gut.

BACKGROUND

There is an existing need to find a composition which induces a high prebiotic effect all along the colon (i.e. up to the descending part of the colon) and having limited side effects due to an adapted fermentation kinetic.

The prebiotic activity has been defined by Gibson and Roberfroid in 1995 (Gibson G R and Roberfroid M, *Dietary Modulation of the Human Colonic Microbiota: Introducing the Concept of Prebiotics,* 1995) and revised in 2004 (Gibson G R, Probert H M, Loo J V, Rastall R A, Roberfroid M, *Dietary Modulation of the Human Colonic Microbiota: Updating the Concept of Prebiotics*), as "a selectively fermented ingredient that allows specific changes both in the composition and/or activity in the gastrointestinal microflora that confers benefits upon host well being and health". It has been shown previously that balancing the microbiota in favour of beneficial bacteria, like Bifidobacteria and Lactobacilli, and to the detriment of harmful bacteria, like coliforms or some species of clostridia, provides some health benefits. To reflect this prebiotic activity of an ingredient or food, a prebiotic index has been designed by Gibson and Roberfroid, taking into account the growth of Bifidobacteria and Lactobacilli as beneficial bacteria and coliforms and clostridia as negative bacteria.

Benefits of prebiotic substances include an improvement in mucosal barrier function, helping to prevent translocation of bacteria to the blood stream; the promotion of beneficial and reduction of pathogenic bacterial subpopulations; the production of short chain fatty acids ('SCFAs'), especially propionate and butyrate, the major energy source for epithelial cells in the large intestine; SOFA also help to regulate sodium and water absorption; and an improvement in host immunity, via interactions between intestinal immune cells and pathogenic bacteria.

Some solutions have been suggested to get a high level of prebiotic effect. It has been proposed to incorporate prebiotic fibres with a high fermentation rate. Most recognised highly fermentable fibres are inulin and fructooligosaccharides (FOS) which have been extensively studied. However, most of the time fructooligosaccharides induce a rapid fermentation in the first part of the colon. This leads to some side effects like bloating, gas production and some social discomfort.

It has also been proposed to incorporate large amounts of prebiotic fibres with a medium fermentation rate. This could display desirable fermentation kinetics, but is generally an issue in terms of palatability and cost of the food products obtained. Moreover, it seems that there is also a saturation of the system when the fibre amount is too high. Finally, increasing the fibre content to high concentration can increase also the risk developing digestive discomfort.

KR20070076231 discloses a method of manufacturing a healthy food product comprising rice bran and buckwheat bran to produce an enhanced immune function, to reduce cholesterol, to regulate blood sugar and to treat and prevent diabetes.

"The combined uses of hull-less barley flour and xylanase as a strategy for wheat/hull-less barley flour and breads with increased arabinoxylan and 1-3, 1-4 beta-D-glucan levels" Trogh et al, Journal of Cereal Science, discloses a bread made with a composite flour with 60% wheat flour and 40% hull-less barley flour.

"Maize bran/oat flour extruded breakfast cereal: a novel source of complex polysaccharides and an antioxidant" Holguin-acuna eta al., Food Chemistry, discloses a maize bran/oat flour extrude breakfast cereal.

"The effects of supplementation of enzyme and probiotic to the rations on some blood parameters of broilers", Midilli et al., Indian Veterinary Journal, discusses the effect of the supplementation of enzyme and probiotics on the blood of broilers.

"Effects of beta-glucanase and xylanase supplementation in pigs fed a diet rich in non-starch polysaccharides: composition of digesta in different prececal segments and postprandial time" Haberer et al., Journal of Animal Physiology and Animal Nutrition, studies the effect of these compounds in pigs.

"Evaluation of baking procedures for incorporation of barley roller milling fractions containing high levels of dietary fibre into bread", Jacobs et al., evaluates baking procedures for incorporating barley fractions containing high levels of dietary fiber into bread.

SUMMARY

Accordingly, the present disclosure seeks to address at least some of the problems associated with the prior art, or at least provide a commercially useful alternative thereto.

Accordingly, in a first aspect there is provided an association of beta-glucans from a first cereal, preferably different from oat, and arabinoxylans from a second cereal different from the first cereal, in an amount of beta-glucans from about 50% to 80% by weight, more preferably from about 51% to 80% by weight, and even more preferably from about 55% to 70% by weight, based upon the total weight of the association.

The present disclosure will now be described further. In the following passages different aspects/embodiments of the disclosure are defined in more detail. Each aspect/embodiment so defined may be combined with any other aspect/embodiment or aspects/embodiments unless clearly indicated to the contrary. In particular, any feature indicated as being preferred or advantageous may be combined with any other feature or features indicated as being preferred or advantageous.

Surprisingly, tit has been found that an association of beta-glucans from a first cereal and arabinoxylans from a second cereal different from the first cereal achieves a high prebiotic effect all along the colon. The combination of the two ingredients presents an enhanced synergistic activity on the prebiotic index which is higher than the one obtained with high fermentation fibres like inulin or FOS, and a longer fermentation kinetic reaching the distal parts of the colon. In addition, it was surprisingly found that the enhanced effect cannot be observed when beta-glucans and arabinoxylans are from a same cereal.

Arabinoxylan (AX) is the main non-starch polysaccharide of cereal grains. These complex carbohydrates occur in cell walls of the starchy endosperm cells and the aleurone layer in most cereals (60-70% (w/w) of the total carbohydrate). Non-endospermic tissues of wheat, particularly the pericarp and testa, can contain a very high concentration of AX (64% (w/w)).

AX consists of a chain of β-1,4-linked xylose units, some of which are mono- or di-substituted with 2, 3 or 2,3-linked arabinose residues. The degree of substitution refers to the arabinose moieties on the xylose backbone and is further also described as A/X ratio, it ranges from 0.10 to over 1.0 depending on cereals and grain fractions. In addition, minor interesting substituents such as hydroxycinnamic acids, and mainly ferulic acid, can be linked to the position 5 carbon of arabinose units.

The substitution and distribution of side chains may be important factors in the physicochemical properties of AX. As for other polymers, the degree of polymerization (DP), i.e. the molecular weight ratio of the polymer relative to the molecular weight of the repeating units, is may also be an important factor in the physicochemical properties of AX.

AX are present in grains in water-extractable and non-water-extractable forms. Wheat endosperm contains 1.5% to 2.5% of arabinoxylan as a component of the endosperm cell walls, of which one third is water-extractable. The rest of arabinoxylan is located in the bran fraction, and is mostly non-water-extractable. Whereas the latter one needs to be extracted from wheat using, for instance, alkali treatment, the water-extractable fraction is readily available in the watery waste streams from the wheat processing (Maes and Delcour 2002). In the current state of the art non-water-extractable AX are extracted by using enzymes (i.e. hemicellulases and endoxylanases) which leads to (partial) hydrolysis of AX and results in a mixture of soluble and non-soluble AX molecules with medium to low molecular weight.

β-Glucans (beta-glucans) are polysaccharides of D-glucose monomers linked by β-glycosidic bonds. β-glucans can vary with respect to molecular mass, solubility, viscosity, and three-dimensional configuration. Some forms of beta-glucans are useful in human nutrition as texturing agents and as soluble fiber supplements, but can be problematic in the process of brewing.

It is already known from the literature that arabinoxylans can act on the organization of the intestinal microbial community. For instance, the International application WO 2006/002495 indicated that short arabinoxylans improve the growth of beneficial bacteria in the colon whereas the International application WO 2010/020639 also demonstrates a prebiotic effect of long chain soluble arabinoxylan. Furthermore, some documents already disclose the use of beta-glucans as a prebiotic (see e.g. WO 2006/005464).

Nevertheless, none of these documents propose to associate beta-glucans and arabinoxylans, let alone to associate beta-glucans from a first cereal and arabinoxylans from a second cereal different from the first cereal, which permits to get a high prebiotic effect along the colon, coupled with limited side effects due to fermentation speed. In particular, none of these documents disclose the required amounts to achieve the beneficial effects.

On the contrary, since many prebiotics are already known from the prior art (inulin, fructooligosaccharides, guar gum, acacia gum, alpha glucan, dextrans, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, and the like), nothing would have lead one skilled in the art to specifically choose beta-glucans and arabinoxylans.

Consequently, according to a first aspect, the present invention is relative to an association of beta-glucans from a first cereal and arabinoxylans from a second cereal different from the first cereal, in an amount of beta-glucans from about 50% to 80% by weight, more preferably from about 51% to 80% by weight, and even more preferably from about 55% to 70% by weight based upon the total weight of the association.

Preferably, said association of beta-glucans from a first cereal and arabinoxylans from a second cereal different from the first cereal, contains an amount of arabinoxylans from about 20% to 50% by weight, more preferably from about 20% to 49% by weight and even more preferably from about 30% to 45% by weight, based upon the total weight of the association.

By "the total weight of beta-glucans and arabinoxylans", it should be understood the total weight of the association, i.e. the total weight of beta-glucans coming from the first cereal and of arabinoxylans coming from the second cereal, excluding the amount of beta-glucans and arabinoxylans that can be provided by other compounds, especially by other cereals.

The term 'cereal', in the context of the present invention, refers to plants of the botanical family of the Poaceae, including but not limited to species such as barley, oat, wheat, rye, spelt, trithordeum, einkorn, rice, maize, triticale, sorghum and any hybrids thereof.

Preferably, the first cereal is barley.

Preferably, the first cereal is different from oat. That is, the first cereal is preferably not oats.

The beta-glucans from the first cereal can come from a concentrated source of said beta-glucan, from a specific part of said first cereal, including starchy endosperm and external layers such as the aleurone one, or from whole grain flour.

Preferably, beta-glucans of the association are provided by a high beta-glucan barley flour. In other words, the association preferably comprises a high beta-glucan barley flour which provides beta-glucans in an appropriate amount.

Methods for isolating beta-glucans to obtain concentrated sources of beta-glucans from barley are well known from one skilled in the art are for example disclosed in U.S. Pat. No. 4,804,545, which is incorporated herein by reference.

According to a specific aspect, the first cereal can be high beta-glucan flour and more advantageously high beta-glucan barley flour.

Within the scope of the invention, "high beta-glucan flour" means flour having a beta-glucan content higher than the one occurring naturally in most of the grains. For instance, the beta-glucan content occurring naturally in barley grain is between 3% and 6.5% of dry matter, whereas a high beta-glucan flour has a beta-glucan content higher than 6.5% of dry matter, preferably higher than 10%, and even more preferably up to 30% of dry matter. This high beta-glucan flour, preferably high beta-glucan barley flour, can either be a whole-grain flour or a refined flour from a variety with enhanced beta-glucan content, e.g. above 6.5% for barley grains, or a cereal flour wherein the starchy endosperm has been partially removed. The removal of the starchy endosperm permits to increase the fiber content.

Within the scope of the invention, "whole grain cereal flour" means flour produced directly or indirectly from cereal whole grains comprising endosperm, bran and germ. The whole grain flour can also be advantageously reconstituted from separate endosperm (for example refined flour), bran and germ respectively in ratios that give to the reconstituted whole grain flour the same composition as whole grain flour directly produced from grains that still retain bran and germ.

High beta-glucan flour can be provided by ConAgra Mills®, under the name Sustagrain® and by Polycell Technologies under the name Barley Balance™.

Preferably, the second cereal is chosen in the group consisting of wheat, rye, spelt, tritordeum, einkorn, rice, maize, any hybrid of these cereals and combination thereof. More preferably, said second cereal is wheat.

The arabinoxylans from the second cereal can come from a concentrated source of arabinoxylans, from a specific part of said second cereal, including cell walls of the starchy endosperm cells and bran layers such as the aleurone layer, or from whole grain flour.

Said arabinoxylans can be supplied by BioActor under the name Naxus or by Witaxos under the name Opti'flor®.

Advantageously, the association of the present invention is an association of beta-glucans from barley and arabinoxylans from wheat, in an amount of beta-glucans from about 50% to 80% by weight, more preferably from about 51% to 80% by weight, and even more preferably from about 55% to 70% by weight, based upon the total weight of the association.

Preferably, the arabinoxylans of the present invention have an average degree of polymerization comprised between 3 and 50, preferably between 10 and 50. As used herein, the degree of polymerization is determined according to Courtin et al. (J. Chromatograph. A866 (2000) 97-104), i.e. by measuring the number of reducing end xylose residues as repeating units.

According to a second aspect, the present invention is relative to a composition comprising an association as defined above, said composition comprising, relative to the total weight of the composition:
  a) 2.8 to 68.0% by weight of beta-glucans, more preferably between 2.9% and 68.0% and even more preferably between 3.1 and 59.5%,
  b) 1.2 to 42.5% by weight of arabinoxylans, more preferably between 1.2% and 41.6% and even more preferably between 1.8 and 38.2%.

Said composition can preferably include additional ingredients including additional thickeners, acidulants, buffers or agents for pH adjustment, pharmaceutically acceptable carrier, preservatives, stabilizers, sugar, sweeteners, texturizers including starch, vitamins, including vitamin D, folate and B12, zinc, calcium, antioxidants or the like.

According to a specific embodiment, said composition is a dry powdered formulation. Preferably, said dry powdered formulation can be prepared by:
  a) mixing the components of said composition in a powdery form.

According to a third aspect, the present invention is relative to a method for the preparation of an association or a composition as defined above, said method comprising:
  1) the step of mixing:
    a) beta-glucans from a first cereal, and
    b) arabinoxylans from a second cereal, different from the first cereal.
Preferably, said beta-glucans and said arabinoxylans are as described above.

Optionally, said method can include a further step 2) of extrusion of the mixing obtained at step 1) and texturizers. Said texturizers can include sugars, proteins and/or expansion regulators like calcium carbonates. Said step 2) can be used to form crisps.

According to a fourth aspect, the present invention is relative to a food product, beverage product or food supplement comprising an association as defined above or the composition as defined above.

Preferably, said food product, beverage product or food supplement, comprises 0.8 to 18.0 grams of arabinoxylans per serving, preferably 1.1 to 4.5 grams of arabinoxylans per serving.

Preferably, said food product, beverage product or food supplement as defined above, comprises between 1.5 to 61.2% by weight of beta-glucans, more preferably between 1.53% and 61.2% and even more preferably between 1.65 and 53.55% by weight of the total weight content of the food product, beverage product or food supplement.

Preferably, the food product is chosen in the group consisting of: biscuit, cereals, crackers, cookies, bread substitutes, bread, cheese, pastas and ready-to-eat meals, and is advantageously chosen in the group consisting of: biscuit, crackers, cookies and bread substitutes, in particular chosen in the group consisting of: biscuit, crackers, cookies and more advantageously is a biscuit or a cookie, even more advantageously is a biscuit.

Preferably, the method for producing a biscuit or a cookie according to the present invention comprises:
  mixing beta-glucans from a first cereal and arabinoxylans from a second cereal different from the first cereal, in an amount of beta-glucans from 50% to 80% by weight, more preferably from about 51% to 80% by weight, and even more preferably from about 55% to 70% by weight, based upon the total weight of the association with at least water, fat and sugar for forming a dough;
  rotary moulding, laminating or extruding the dough for shaping the biscuit or forming the cookie;
  baking the biscuit or the cookie.

Before baking, the biscuits can be glazed so that they gain a shiny appearance. Therefore, the method can comprise an optional additional step of glazing the shaped biscuit. The biscuit can be glazed with an aqueous glazing, comprising milk powder and/or icing sugar and/or buffering agent such as sodium bicarbonate, sodium hydroxide.

Advantageously, the glazing comprises skimmed milk powder. Still advantageously, the glazing comprises starchy icing sugar, i.e. sucrose natural sweetener characterised by its fine granulometry obtained by milling crystal sugar and added with starch as an anti-agglomerating agent.

Baking is advantageously carried out until the moisture content of the baked biscuit/cookie (final product) is 0.5 wt. % to 5.0 wt. %, for example by baking during 12 min. at a temperature between 150° C. and 170° C.

After baking, the baked biscuits are cooled down on an open belt, i.e. a belt that is not covered, a cooling tunnel is preferably not used because there is a too much temperature differential between the input and the output, what causes checking (failure) in the biscuit. The biscuits are then packaged, for example biscuits are packaged into wrappers containing 50 g of biscuits and the wrappers are gathered in a packet that is designed to contain 6, 8 or 12 wrappers. Advantageously, the biscuits can be packaged in wrappers so that one wrapper contains one serving.

More generally, the biscuit according to the invention may comprise additional cereal bran and/or cereal germ. In case there are additional cereal bran and cereal germ, the bran and the germ come from different cereals which can be chosen in the group consisting of wheat, barley, rye, spelt, oat, rice, maize or a mixture thereof.

Other ingredients that can be mixed with the cereal flour and water for forming the dough are: emulsifier, leavening agents and the like. Emulsifier can be soybean lecithin, diacetyl tartaric ester of monoglyceride, sodium stearoyl lactylate. Leavening agent can be ammonium bicarbonate, sodium bicarbonate, sodium pyrophosphate acid or a mixture thereof. Other ingredients can also be vitamins or minerals such as vitamin B1, vitamin E, vitamin PP, iron and magnesium and a mixture thereof. Still other ingredients can be salt, flavouring agents, cocoa powder, solid pieces, milk and dairy derivatives, honey.

Flavouring agents can be in powder form or liquid form. Solid pieces may be chocolate drops, fruit pieces, nuts like hazelnut (preferably hazelnut pieces), extruded cereal, etc. Chocolate drops are pieces of solid chocolate. "Chocolate" is understood a meaning either "dark chocolate", "milk chocolate" or "white chocolate".

Within the scope of the invention, "fruit pieces" means pieces of any sweet, edible part of a plant that resembles fruit, for example raisin, fig, prune, orange, cranberry, blueberry, raspberry, strawberry, apricot, blackcurrant, redcurrant, peach, pear, kiwi, banana, apple, lemon, pineapple, tomato. These pieces of fruit are either dried or processed.

The biscuit may further comprise wholegrain cereal flakes, preferably at most 16 wt. %, more preferably at most 11 wt. %, still more preferably at most 8 wt. % wholegrain cereal flakes over the total weight of the biscuit, for example wholegrain oat flakes or malted wholegrain rye flakes. An excess of flakes, i.e. over 11 wt. %, will give to the biscuit an unexpected aspect, i.e. aspect of granola biscuit and a denser product, that can draw away potential consumers.

The food product can also be a cookie comprising a biscuit part and a filling part.

Preferably, the biscuit part includes at least one biscuit as described above.

This cookie can be a filling over biscuit type biscuit, the biscuit being produced with the method described above and the filling being layered on the biscuit before or after baking. This cookie can still be a sandwich cookie, i.e. a cookie wherein a layer of filling lies between two layers of biscuits, the biscuits being distinct. The biscuits can be produced with the method described above. The sandwich cookie is most commonly assembled after baking the biscuits.

The filling part of the cookie can still be at least partly enclosed by the biscuit part. In this latter case, the biscuit part builds a continuous biscuit and comprises a cavity therein for receiving the filling part. The cookie can still be formed in more than one step, with the biscuit part formed with its cavity therein and the filling part being injected into the cavity before or after baking the biscuit part.

The filling part may comprise at least one of the following ingredients: fat, sugar, water, starch, emulsifier, milk and dairy derivates, flavouring agents, fruit powder, fruit pieces, cocoa powder, chocolate drops, seeds.

The beta-glucan from the first cereal and the arabinoxylan from the second cereal can be both present in the biscuit part, both present in the filling part, one in the filling part and one in the biscuit part or both in the filling and in the biscuit part.

Preferably, the beta-glucan from the first cereal is included in majority in the biscuit part. More preferably, the all of the beta-glucan from the first cereal is included in the biscuit part.

Preferably, the majority of the arabinoxylan from the second cereal is included in the filling part.

In a preferred embodiment, the majority of the beta-glucan from the first cereal is in the biscuit part and the majority of the arabinoxylan from the second cereal is in the filling part. Such a distribution provides a surprisingly enhanced organoleptic property in the final cookie.

By the "majority of the beta-glucan from the first cereal" one should understand at least 60%, preferably at least 70%, 80%, 90% and even more preferably at least 95% by weight of total weight of beta-glucan from the first cereal.

By the "majority of the arabinoxylan from the second cereal" one should understand at least 60%, preferably at least 70%, 80%, 90% and even more preferably at least 95% by weight of total weight of the arabinoxylan from the second cereal.

By "cereals", one should understand, for example, breakfast cereals and flours.

Preferably, the beverage product is chosen in the group consisting of milk, non-alcoholic soft drinks including sugar-free drinks, fruit juices, coffee, tea, chocolate beverages and soups.

The food supplement can be for example in the form of oral tablets, capsules, powder or oral liquid form.

According to a fifth aspect, the invention is relative to a non-therapeutic use of an association, a composition, a food product, a beverage product or a food supplement as defined above to improve the microbiota balance in gut and therefore digestive health.

By "to improve microbiota balance" it should be understood to increase the prebiotic index, i.e. to promote the growth or mucosal adhesion of beneficial bacteria (e.g. Bifidobacteria and Lactobacilli) in intestine or inhibits the growth or mucosal adhesion of harmful bacteria (e.g. Coliforms and Clostridia) in the intestine.

By "improved activity" or "improved index", one should understand an activity/index, which is enhanced/increased when compared to the activity/index of each compound of the association alone, preferably an activity which is enhanced/increased when compared to the sum of the individual activity/index of each compound of the association.

By "improved", "enhanced" or "increased", one should understand an increase of at least a factor of 1.2, preferably of at least a factor of 1.5, 1.8, 2, 2.5 and even more preferably of at least a factor of 3 when compared with a reference.

In the meaning of the present invention, said prebiotic index can be calculated as follows:

$$PI_{tx}=((Bifido_{tx}/Bifido_{t0})+(Lacto_{tx}/Lacto_{t0})-(Coli_{tx}/Coli_{t0})-(Clos_{tx}/Clos_{t0}))/(Tot_{tx}/Tot_{t0})$$

with:
- $PI_{tx}$=Prebiotic Index after treatment (t0=baseline value, tx=value at time x)
- Bifido=bifidobacteria concentration at time tx/bifidobacteria concentration at time t0
- Lacto=lactobacilli concentration at time tx/lactobacilli concentration at time t0
- Coli=fecal coliforms concentration at time tx/fecal coliforms concentration at time t0
- Clos=clostridia adhered at time tx/clostridia concentration at time t0
- Tot=total bacteria concentration at time tx/total bacteria concentration at time t0

Preferably, said non-therapeutic use of an association, a composition, a food product, a beverage product or a food supplement as defined above to improve the microbiota balance in gut is useful for weight management of a non-obese subject, to avoid gastro-intestinal discomfort, to enhance muscle mass in a non sick person, more preferably for weight management of a non-obese subject and to avoid gastro-intestinal discomfort.

According to a sixth aspect, said invention is relative to an association, a composition, a food product, a beverage product or a food supplement as defined above, for its use as a medicament.

The invention is also relative to a method for treating and/or preventing a disease in a subject in need thereof comprising the step of administering an effective amount of an association, a composition, a food product, a beverage product or a food supplement as defined above to said subject.

According to the present invention, an "effective amount" of a composition is one which is sufficient to achieve a desired biological effect, in this case preventing or treating a pathology chosen in the group consisting of: constipation, inflammatory bowel syndrome, inflammatory bowel disease, osteoporosis, weight management of an obese subject, cancers particularly colon cancers, diabetes, and conditions associated with oxidative stress and/or cardiovascular diseases.

It is understood that the effective dosage will be dependent upon the age, sex, health, and weight of the recipient, kind of concurrent treatment, if any, frequency of treatment, the route of administration and the nature of the effect desired. The preferred dosage can be tailored to the individual subject, as is understood and determinable by one of skill in the art, without undue experimentation.

As an example, an effective amount of the association of beta-glucans from a first cereal and arabinoxylans from a second cereal as defined before corresponds to an administration of 170 mg/kg of body weight per day, preferably of 50 mg/kg of body weight per day.

Preferably, the invention is relative to an association, a composition, a food product, a beverage product or a food supplement as defined above, for its use as a medicament for the prevention or the treatment of a pathology chosen in the group consisting of: constipation, inflammatory bowel syndrome, inflammatory bowel disease, osteoporosis, weight management of an obese subject, cancers particularly colon cancers, diabetes, and conditions associated with oxidative stress and/or cardiovascular diseases.

For instance, osteoporosis can be prevented or treated by administering the composition, food product, beverage product or food supplement as defined above, to increase absorption of vitamins and nutrients in an individual's intestine and colon, such as vitamin D, zinc or calcium to assist in improving bone composition and function.

Said vitamin D, zinc or calcium can be provided by the composition, food product, beverage product or food supplement itself, or from other food or complement sources.

Weight management of an obese subject can be achieved by administering the composition, food product, beverage product or food supplement as defined above, which permits to enhance the satiety effect and thus to avoid overeating.

Prevention or treatment of diabetes can be achieved by administering the composition, food product, beverage product or food supplement as defined above, which permits to reduce insulin resistance and decrease blood glucose concentration.

The invention is also relative to the use of an association, a composition, a food product, a beverage product or a food supplement as defined above, in the manufacture of a medicament for the prevention or the treatment of a pathology chosen in the group consisting of: constipation, inflammatory bowel syndrome, inflammatory bowel disease, osteoporosis, weight management of an obese subject, cancers particularly colon cancers, diabetes, and conditions associated with oxidative stress and/or cardiovascular diseases.

According to a seventh aspect, the invention is relative to an association of beta-glucans from a first cereal and arabinoxylans from a second cereal different from the first cereal in an amount of beta-glucans from about 50% to 80% by weight, more preferably from about 51% to 80% by weight, and even more preferably from about 55% to 70% by weight, based upon the total weight of the association, as a combined preparation for simultaneous, separate, or sequential use for preventing and/or treating a pathology chosen in the group consisting of: constipation, inflammatory bowel syndrome, inflammatory bowel disease, osteoporosis, weight management of an obese subject, cancers particularly colon cancers, diabetes, and conditions associated with oxidative stress and/or cardiovascular diseases.

Preferably, said beta-glucans and said arabinoxylans are as described above.

According to a further aspect there is provided a biscuit comprising a first cereal comprising beta-glucans and a second cereal comprising arabinoxylans, wherein the second cereal is different from the first cereal, and wherein the ratio of beta-glucans in the first cereal to arabinoxylans in the second cereal is from 1:1 to 4:1, preferably 11:9 to 7:3.

More preferably, there is provided a biscuit comprising oats or barley as a source of beta-glucans and wheat as a source of arabinoxylans, wherein the ratio of beta-glucans in the oat or barley to arabinoxylans in the wheat is from 1:1 to 4:1, preferably 11:9 to 7:3.

According to a further aspect there is provided a sandwich cookie comprising at least one biscuit portion and a filling portion, wherein the sandwich cookie comprises a first cereal comprising beta-glucans and a second cereal comprising arabinoxylans, wherein the second cereal is different from the first cereal, wherein the first cereal is predominantly in the one or more biscuit portions (preferably at least 60%) and wherein the second cereal is predominantly in the filling (preferably at least 60%) and wherein the ratio of beta-glucans in the first cereal to arabinoxylans in the second cereal is from 1:1 to 4:1, preferably 11:9 to 7:3. Preferably the first cereal is oats or barley and preferably the second cereal is wheat.

According to a further aspect there is provided a sandwich cookie comprising at least one biscuit portion and a filling portion, wherein the one or more biscuit portions comprise a first cereal comprising beta-glucans and the filling portion comprises a second cereal comprising arabinoxylans, wherein the second cereal is different from the first cereal, and wherein the ratio of beta-glucans in the first cereal to arabinoxylans in the second cereal is from 1:1 to 4:1, preferably 11:9 to 7:3.

More preferably, there is provided a sandwich cookie comprising at least one biscuit portion and a filling portion, wherein the one or more biscuit portions comprise oats or barley as a source of beta-glucans and the filling portion comprises wheat as a source of arabinoxylans, wherein the ratio of beta-glucans in the oat or barley to arabinoxylans in the wheat is from 1:1 to 4:1, preferably 11:9 to 7:3.

Preferably the biscuit or sandwich cookie described about contain only wheat and oats or barley as cereal ingredients. It has been found that wheat is an excellent source of arabinoxylans and can provide higher levels than other cereals. It has also been found that oats and barley are excellent sources of beta-glucans and can provide higher levels than other cereals.

Preferably each biscuit or cookie comprises from 0.5 to 2 g of arabinoxylans and from 0.75 to 3 g of beta-glucans. A typical biscuit weighs 12.5 g and a typical sandwich cookie weights 25 g. Accordingly, preferably the biscuit or cookie contains from 2-16 wt % of arabinoxylans (preferably from wheat) and from 3-24 wt % of beta-glucans (preferably from oat or barley). More preferably the biscuit or cookie contains from 4-12 wt % of arabinoxylans (preferably from wheat) and from 9-18 wt % of beta-glucans (preferably from oat or barley).

It has been found that the foregoing biscuits and sandwich cookies have an excellent organoleptic property, while at the same time are especially suitable for the non-therapeutic and medical uses discussed herein. Surprisingly, these biscuit and cookie serve as excellent products for improving the colonic health of the consumer. Moreover, the particular use of wheat, together with either oats or barley has been found to provide an improved prebiotic effect, as demonstrated in the examples.

The foregoing aspects may be freely combined with any of the foregoing aspects disclosed herein.

FIGURES

The present disclosure will be described in relation to the following non-limiting figures, in which.

EXAMPLES

The present disclosure will now be described in relation to the following non-limiting examples.

Example 1

In Vitro Effects of High Beta-Glucan Barley Flour and AX on Microbiota

The effect of the same concentrations of whole barley flour and wheat AX on microbiota versus inulin (positive control) and cellulose (negative control) was investigated in a simple in vitro model. For this study, arabinoxylans presenting a degree of polymerization comprised between 3 and 50 were used. The typical short-term screening assay consists of the sequential incubation (in triplicate) of a representative dose of the ingredients under simulated conditions for:
1. Stomach (pH 2, pepsin);
2. Small intestine: addition of pancreatic enzymes and bile salts;
3. Large intestine with representative bacterial inoculum in basal medium. This bacterial inoculum derived from an already "in vitro" adapted microbial community from the ascending colon compartment in the SHIME system.

Figure 1:
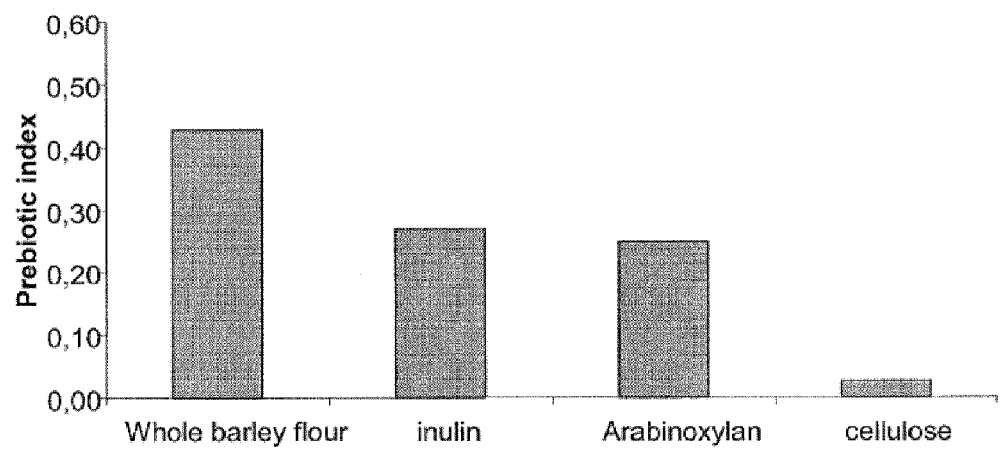
FIG. 1 shows the prebiotic effect of whole barley flour, inulin, AX and cellulose obtained with a Simulator of the Human Intestinal Microbial Ecosystem (SHIME) in vitro model.

The results presented in FIG. 1 show that AX has a mean Prebiotic Index close to inulin (0.25 and 0.27, respectively) whereas whole barley flour, which contains both beta-glucan 56.0% of the association of beta-glucan+AX from said whole barley flour) and AX (44.0% of the association of beta-glucan+AX from said whole barley flour) displayed higher activity compared to the two latter ingredients (0.43).

Example 2

Figure 2:
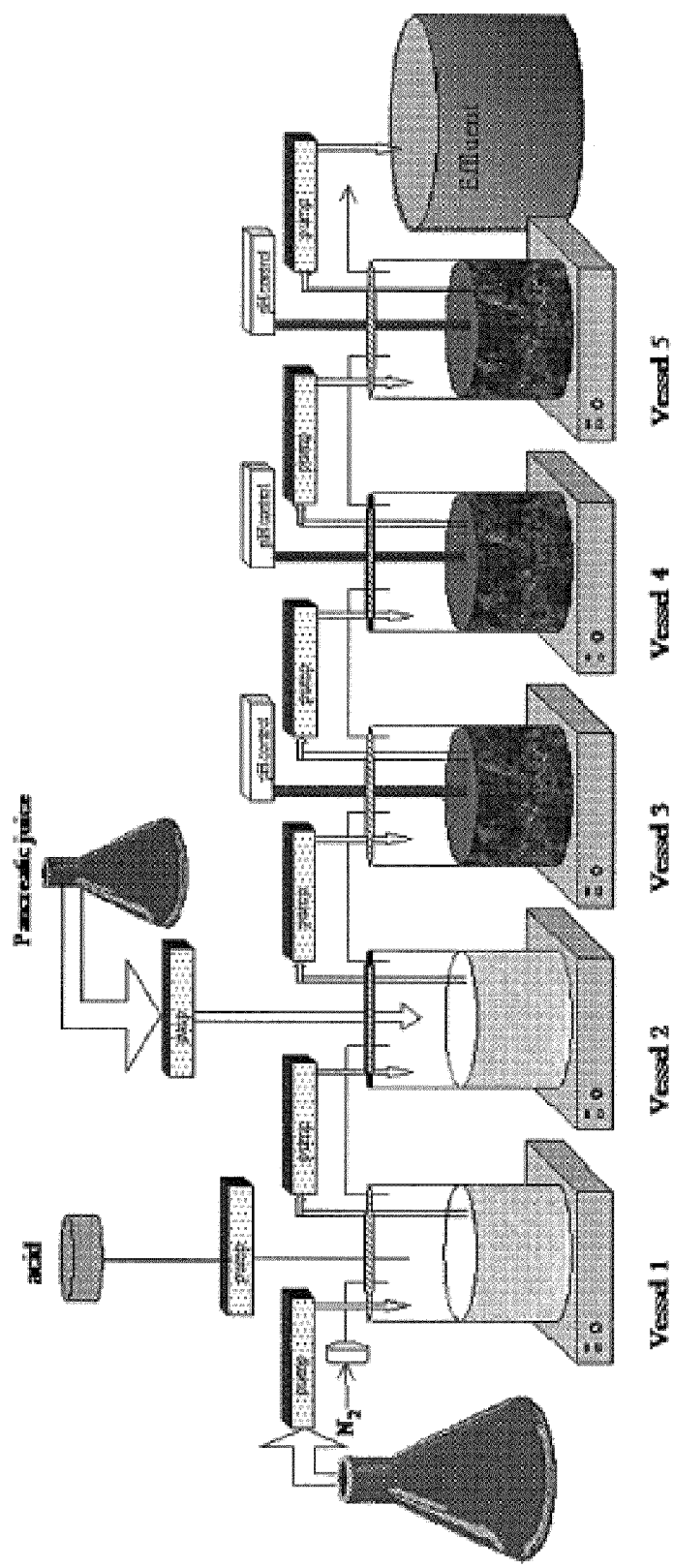
FIG. 2 shows the standard setup of the Simulator of the Human Intestinal Microbial Ecosystem (SHIME), consisting of 5 sequential reactors which simulate the different regions of the human intestinal tract.

Effects of High Beta-Glucan Barley Flour and AX on Microbiota Measured with a Simulator of the Human Intestinal Microbial Ecosystem In Vitro Model Some additional results were obtained with a Simulator of the Human Intestinal Microbial Ecosystem in vitro model (SHIME; Molly et al, 1993; Possemiers et al, 2008). The SHIME consists of a succession of five reactors simulating the different parts of the human gastrointestinal tract (see FIG. 2).

The association of wheat AX and high beta-glucan barley flour, wheat AX alone, high beta-glucan barley flour alone, inulin and cellulose, were tested in the present in vitro model. The same AX as described in example 1 were used.

In this experiment, the model was fed with 5 g of fibres per day, divided into 3 doses. For the association, 2.25 g of AX from wheat and 2.75 g of beta-glucans from barley were used (proportions (45/55)).

An increase in Bifidobacteria and Lactobacilli, a slight decrease in Clostridia and no modification of Coliforms was observed, mainly with high beta-glucan barley flour alone and in combination with wheat AX.

This allowed calculating the prebiotic index in the three parts of the colon (ascending, transverse and descending which is the more distal part). The values obtained are displayed in the table 1 below:

TABLE 1

| Prebiotic index value | Wheat AX | High beta-glucan barley flour | Association wheat AX + high beta-glucan barley flour (45/55) | Inulin | Cellulose |
| --- | --- | --- | --- | --- | --- |
| Ascending colon | 0.28 | 11.42 | 7282 | 1.69 | −1.31 |
| Transverse colon | −0.09 | 5.06 | 4023 | 3.21 | −13.18 |
| Descending colon | 0.48 | −2.99 | 8109 | 4.11 | −9.38 |

The values obtained in this experiment show that the prebiotic index obtained for the association of wheat AX and high beta-glucan barley flour are much higher than those obtained for wheat arabinoxylans or high beta-glucan barley flour (45/55) alone and much higher than inulin. Moreover, the values obtained with the association are also much higher than the sum of the values obtained for arabinoxylans or high beta-glucan barley flour alone. Then it appears that the two ingredients wheat AX and high beta-glucan barley flour have a synergistic effect on the gut microbiota.

Moreover, from the prebiotic index values and the short-chain fatty acid production, it appears that this combination of fibres has an effect spread all along the colon and reaching the more distal part of it (descending colon).

The present fibre mix, combining wheat arabinoxylans and high beta-glucan barley flour display a synergic effect on microbiota balance, superior to the one of inulin. Moreover, the effect is prolonged and can be quantified in the distal parts of the colon.

In another experiment, other types of beta-glucan sources were tested as well as various ratios of AX and beta-glucan:
  A high beta-glucan oat flour alone or combined with wheat AX in order to provide 2.25 g of AX from wheat and 2.75 g of beta-glucans from oat;
  A mix of wheat AX and barley beta-glucans providing for 5 g of fibers fed to the model, 1.5 g were AX from wheat and 3.5 g were beta-glucans from barley.

In this trial, wheat AX, wheat AX combined with high beta-glucan oat flour and wheat AX combined with high beta-glucans barley flour (30/70) displayed a high growth of bifidobacteria. In general, this effect is mainly present in ascending colon. In the same way, high beta-glucan barley flour and the combination of wheat AX and high beta-glucan barley flour (30/70) induced a great increase in lactobacillus population (+2 to 3 logs of increase). Again for this experiment, the prebiotic index has been calculated for these different ingredients in the three parts of the colon. The results are presented in Table 2 below:

TABLE 2

| Prebiotic index value | Wheat AX | High beta-glucan barley flour | Association wheat AX + high beta-glucan barley flour (30/70) | High beta-glucan oat flour | Association wheat AX + high beta-glucan oat flour (45/55) | Inulin | Cellulose |
|---|---|---|---|---|---|---|---|
| Ascending colon | 14.36 | 70.61 | 287.92 | 3.30 | 14.53 | 3.83 | −17.37 |
| Transverse colon | 3.49 | 74.47 | 409.22 | 3.71 | 5.38 | 4.02 | −11.71 |
| Descending colon | 7.17 | 146.43 | 109.78 | 10.27 | 14.52 | 2.24 | −5.90 |

This data shows that:
  The synergy of wheat AX and high beta-glucan barley flour is still present with a ratio of wheat AX and barley beta-glucans of 30/70
  When wheat AX and high beta-glucan oat flour are combined there is no synergy of these two ingredients for prebiotic activity Thus, it can be concluded that combining wheat AX and barley flour high in beta-glucans leads to a synergistic activity on gut microbiota composition. This effect is observed on a wide range of wheat AX to barley beta-glucan ratio. This effect appears to be supported with barley flour; beta-glucans from oat do not lead to similar synergy between the two fibers. Finally, it is confirmed that the mix wheat AX and high beta-glucan barley flour induces a prebiotic on the whole length of the colon reaching the most distal part of it and this activity is much higher compared to inulin one.

Example 3

Biscuit According to the Invention

Rotary moulded biscuits containing the mix of fibres of the invention have been produced at pilot scale. Here is the biscuit formula:

| Ingredient list | Percentage in formula |
|---|---|
| Whole grain Flour | 2.77% |
| Oat flakes and crisps | 15.80% |
| Vegetable oil | 11.06% |
| Soy lecithin | 0.4% |

-continued

| Ingredient list | Percentage in formula |
|---|---|
| Wheat arabinoxylan flour | 7.9% |
| High beta glucan Barley flour | 25.87% |
| sucrose | 13.43% |
| Leavening agents | 2.89% |
| Salt | 0.34% |
| Water | 19.16% |

Said dough before baking contains 7.5% of beta-glucan from barley and 6.7% of arabinoxylan from wheat.

Example 4

Sandwiched Cookies According to the Invention

Rotary sandwiched cookies containing the mix of fibres of the invention have been produced at pilot scale. Here is the cookie formula of the sandwich cookie:

| Ingredient list | Percentage in formula |
|---|---|
| Whole grain flours mix | 18.7% |
| Oat flakes and crisps | 10.1% |
| Vegetable oil | 9.8% |
| Soy lecithin | 0.1% |
| High beta-glucan barley flour | 34% |
| sucrose | 15.4% |
| Leavening agents | 0.8% |
| Flavour | 0.3% |
| Salt | 0.2% |
| Water | 10.6% |

And the filling formula of the sandwich cookie can be:

| Ingredient list | Percentage in formula |
|---|---|
| Cocoa powder | 15.4% |
| Sugar | 43.8% |
| Vegetable oil | 26.4% |
| Soy lecithin | 0.1% |
| Wheat arabinoxylan flour | 14% |

Said dough biscuit before baking contains 6.92% of beta-glucan from barley and 3.48% of arabinoxylan from wheat in the filling of the dough biscuit before baking.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

The invention claimed is:

1. A method of improving the microbiota balance in human gut and digestive health in a subject, the method comprising administering to the subject an effective amount of a first cereal comprising high beta-glucan barley flour and a second cereal comprising wheat, wherein the ratio of beta-glucans in the first cereal to arabinoxylans in the second cereal is from 1:1 to 4:1.

2. A method according to claim 1, wherein the ratio of the beta-glucans in the first cereal to arabinoxylans in the second cereal is from 11:9 to 7:3.

3. A method according to claim 1, wherein the arabinoxylans have an average degree of polymerization between 3 and 50.

4. A method according to claim 3, wherein the arabinoxylans have an average degree of polymerization between 10 and 50.

5. A method according to claim 1, wherein said first cereal and said second cereal are provided in the form of a biscuit.

6. A method according to claim 5, wherein the biscuit comprises from 2-16 wt % of arabinoxylans and from 3-24 wt % of beta-glucans.

7. A method according to claim 6, wherein the biscuit comprises from 4-12 wt % of arabinoxylans and from 9-18 wt % of beta-glucans.

8. A method according to claim 5, comprising between 1.5 to 61.2% by weight of beta-glucans based upon a total weight content of the biscuit.

9. A method according to claim 8, comprising between 1.53 to 61.2% by weight of beta-glucans based upon a total weight content of the biscuit.

10. A method according to claim 9, comprising between 1.65 to 53.55% by weight of beta-glucans based upon a total weight content of the biscuit.

11. A method according to claim 5, wherein the biscuit is a sandwich cookie comprising at least one biscuit portion and a filling portion, wherein the first cereal is predominantly in the one or more biscuit portions and wherein the second cereal is predominantly in the filling.

* * * * *